(12) United States Patent
Di Leo et al.

(10) Patent No.: US 10,716,805 B2
(45) Date of Patent: Jul. 21, 2020

(54) FORMULATION FOR RELEASE OF NITRIC OXIDE

(71) Applicant: Glanotech Limited, London (GB)

(72) Inventors: Gioacchino Di Leo, Rome (IT); Luciano Caglioti, Rome (IT); Alberto Boffi, Rome (IT); Luciana Mosca, Rome (IT); Robert Giovanni Nisticò, Rome (IT)

(73) Assignee: Glanotech Limited, London (GB)

( * ) Notice: Subject to any disclaimer, the term of this patent is extended or adjusted under 35 U.S.C. 154(b) by 52 days.

(21) Appl. No.: 15/925,198

(22) Filed: Mar. 19, 2018

(65) Prior Publication Data

US 2019/0282610 A1 Sep. 19, 2019

(51) Int. Cl.
*A61K 33/00* (2006.01)
*A61P 15/10* (2006.01)

(52) U.S. Cl.
CPC .............. *A61K 33/00* (2013.01); *A61P 15/10* (2018.01)

(58) Field of Classification Search
None
See application file for complete search history.

(56) References Cited

U.S. PATENT DOCUMENTS

| 7,048,951 | B1* | 5/2006 | Seitz | A61K 9/0014 424/718 |
| 2011/0287113 | A1* | 11/2011 | Davis | A61K 9/0014 424/718 |
| 2013/0059017 | A1 | 3/2013 | Perricone | |
| 2013/0089629 | A1 | 4/2013 | Beijer et al. | |

FOREIGN PATENT DOCUMENTS

| WO | WO-1999044622 A1 | 9/1999 |
| WO | WO-2008153762 A2 | 12/2008 |
| WO | WO-201102265 A1 | 1/2011 |

OTHER PUBLICATIONS

Agmo, A., "Male Rat Sexual Behavior," Brain Res Brain Protoc 1(2):203-209, Brain Research Protocols, Elsevier, Netherlands (1997).
Broniowska, K.A., et al., "The chemical biology of S-nitrosothiols," Antioxid Redox Signal 17(7):969-980, Mary Ann Liebert, (2012).
Burnett, A., "Role of Nitric Oxide in the Physiology of Erection," Biology of Reproduction 52(3):485-489, Oxford Academic, United Kingdom (1995).
Cayatte, A., et al., "Chronic inhibition of nitric oxide production accelerates neointima formation and impairs endothelial function in hypercholesterolemic rabbits," Arterioscler Thromb 14(5):753-759, American Heart Association, United States (1994).
Fukoto, JM., et al., "A comparison of the chemistry associated with the biological signaling and actions of nitroxyl (HNO) and nitric oxide (NO)," J Inorg Biochem 118:201-208, Elsevier, Netherlands (2013).
Fulton, D., et al., "Post translational control of endothelial nitric oxide synthase: why isn't calcium/calmoduline enough?," Journal of Pharmacology and Experimental Therapeutics 220:815-861, American Society for Pharmacology and Experiemntal Therapeutics, United States (2001).
Furchgott, R.F., et al., "The obligatory role of endothelial cells in the relaxation of arterial smooth muscle by acetylcholine," Nature 288:373-376, Nature Publishing Group, United Kingdom (1980).
Italiano, G., et al., "A Simplified In Vitro Preparation of the Corpus Cavernosum as a tool for Investigating Erectile Pharmacology in the Rat," Pharmacological Research 30(4):325-334, Italian Pharmalogical Society, Italy (1994).
Ignarro, L.J., "Endothelium-derived nitric oxide: actions and properties," FASEB J. 3(1):31-6, Federation of American Societies for Experimental Biology, United States (1989).
Marletta, M., et al., "Nitric oxide Synthase Structure and Mechanism," the Journal of Biological Chemistry 268(17):12231-12234, American Society for Biochemistry and Molecular Biology, United States (1993).
Moncada, S., et al., "The L-arginine-nitric oxide pathway," New England Journal of Medicine 329(27):2002-2012, Massachusetts Medical Society, United States (1993).
Namazi, M.R., et al., "Nitric Oxide donors as potential additions to anti-alopecia areata armamentarium," Inflamm Res 52(6):227-229, Springer-Link, United States (2003).
Qin, M., et al., "Nitric Oxide Releasing Nanoparticles prevent Propionibacterium acnes induced inflammation by both clearing the organism and inhibiting microbial stimulation of the innate immune response," J. Invest Dermatol 135(11):2723-2731, Elsevier, Netherlands (2015).
Palmer, R.M., et al., "Nitric oxide release accounts for the biological activity of endothelium-derived relaxing factor," Nature 327:524-526, Nature Publishing Group, United Kingdom (1987).
Rajfer, J., et al., "Nitric oxide as a mediator of relaxation of the corpus cavernosum in response to nonadrenergic, noncholinergic neurotransmission," NEJM 326(2):90-94, Massachusetts Medical Society, United States (1992).
Schouten, W.R., et al., "Anal Fissure: New Concepts in Pathogenesis and treatment," Scandinavian Journal of Gastroenterology 31(218):78-81, Taylor & Francis Online, United States (1996).
Seidler, M., et al., "In vitro effects of a novel class of nitric oxide (NO) donating compounds on isolated human erectile tissue," Eur Urol 42(5):523-528, Elsevier, Netherlands (2002).
Smith, B.C., et al., "Mechanisms of S-nitrosothiol formation and selectivity in nitric oxide signaling," Curr Opin Chem Biol 16(15-6):498-506, Elsevier, Netherlands (2012).
Souto, S., et al., "Vascular modifications of the clitoris induced by topic nitric oxide donor gel—preliminary study," J. Sex Med. 8(2):484-488, Elsevier, Netherlands (2011).
Toda, N., et al., "Nitric oxide and penile erectile function," Pharmacology & Therapeutics 106:233-266, Elsevier, Netherlands (2005).

* cited by examiner

*Primary Examiner* — Jake M Vu (74) *Attorney, Agent, or Firm* — Sterne, Kessler, Goldstein & Fox P.L.L.C.

(57) ABSTRACT

A composition for releasing nitric oxide which provides a rapid release of nitrogen monoxide, and also allows formation of S-nitrosothiol compounds which provide a slower extended release of nitrogen monoxide. A composition kit includes two components that are mixed together to initiate nitric oxide release. The kit includes: a liquid phase comprising a solvent and at least one reducing agent; and a solid phase comprising a nitrate and/or nitrite salt, copper ions and at least one thiol. A method of treating sexual dysfunction involves topically applying the composition to an area of the subject to be treated.

14 Claims, 3 Drawing Sheets

FORMULATION FOR RELEASE OF NITRIC OXIDE

FIELD OF THE INVENTION

The present invention relates to the field of pharmaceutical formulations.

In particular, it relates to a new formulation for the release of nitric oxide.

BACKGROUND OF THE INVENTION

Biological Functions of Nitric Oxide (NO)

Nitric oxide (NO) is a ubiquitous molecule with various biological functions, based mainly on its vasodilatory effect (Ignarro et al., 1989).

NO is a diffusible gas that can be classified as a chemical messenger, capable of:
  modulating the activity of specific NO-binding enzymes: for instance guanylate cyclase, which induces the formation of the second cGMP messenger (cGMP causes vasodilation in vascular smooth muscle);
  binding and modifying enzymes and ion channels (nitrosylation), which thereby change their activity.

NO is produced by the enzyme NO synthase, which degrades arginine and citrulline, releasing an NO molecule (Rajfer et al., 1992).

There are various isoforms of NO synthase, which can be classified schematically according to their basal activity.

NO is rapidly degraded/inactivated; it is therefore, basically a "locally acting" second messenger it differs from classic second messengers in that it can perform its effects also on cells (Fulton et al., 2001; Furchgott et al., 1980).

Biological Role of NO in the Physiology of Penile Erection

Penile erection is a physiological phenomenon resulting from a haemodynamic event and a neurogenic event.

It is a haemodynamic event in that the degree of erection depends on the balance between arterial inflow (pudendal arteries) and venous outflow (superficial veins, deep dorsal vein, and the veins of the corpora cavernosa).

It is a neurogenic event in that the penis is flaccid when the arterial and venous inflow are equally balanced; it is tumescent when the arterial inflow increases and the venous outflow decreases.

In the flaccid penis the main system responsible for maintaining vasoconstriction and contraction of the smooth muscle of the corpora cavernosa is the sympathetic nervous system (low blood flow to the penis); in the erect penis the system that maintains dilatation of the arteriole and relaxation of the trabecular smooth muscle is the parasympathetic nervous system.

Biochemistry of Penile Erection

As indicated above, at the time of erection the muscles of the corpora cavernosa of the penis are relaxed and, at the same time, the arterial flow increases and the venous blood flow decreases.

This mechanism is regulated by a nerve component, which makes erection a neurovascular process involving a series of transmitters and modulators.

A central role in this process is performed by the nitric oxide (NO) molecule, produced in its capacity as a mediator in response to stimulation from non-adrenergic, non-cholinergic (NANC) nerve fibres present within the smooth muscle of the corpora cavernosa of the penis and also present in the arteries and veins (Palmer et al., 1987).

The NO mediator is able to cause the corpora cavernosa to relax, a fundamental event for the purposes of erection.

During the penile erection process the production of NO by NO synthase of endothelial origin (eNOS) increases, which has a vasodilatory effect on the vascular endothelium.

This happens in physiological conditions, in which the endothelium is not affected by any pathology.

In pathological conditions, however, the biochemical pathways for NO production are disrupted (Cayatte et al., 1994). This causes biochemical changes responsible for the altered homeostasis that causes penile erection disorders.

It is believed, moreover, that during erection the primary factor involved is production of NO by the isoform of neuronal NO synthase (nNOS) following nerve stimulation, causing a transient increase in blood flow and increased blood circulation in the penis and sinusoidal spaces.

Next, a further, substantial production of NO by eNOS occurs, making an effective erection possible.

The NO mediator, which arrives by diffusion into the smooth muscle cells of the corpora cavernosa, activates the enzyme guanylate cyclase (GC), which is in turn responsible for producing a cyclic second messenger, cGMP.

These cyclic nucleotides are subjected to a process of hydrolysis by phosphodiesterase (PDE) isoenzymes, and, particularly in the corpora cavernosa of the penis, the PDE 5 isoform (pharmacological target of Viagra-like drugs that inhibit phosphodiesterase) (Moncada et al., 1993).

Over the last few years, however, it has become increasingly clear that many of the cellular actions of NO take place also in cGMP-independent mode; in-vivo reactions have been described between NO and oxygen, iron, the haem group, proteins containing thiol groups, DNA and some amines subject to S-nitrosylation (Marietta et al., 1993).

In view of the above, a system that increases the availability of NO is highly desirable in many pathophysiological conditions, particularly where there is sexual dysfunction.

In fact, in normal conditions, the release of NO onto the endothelial walls of the blood vessels promotes the vasodilatory effect, which causes penile erection, among other things.

Therefore, to improve the process of penile erection, particularly in cases where it is impaired, it is highly desirable to provide NO, chiefly in topical form, in order to produce vasodilatory effects similar to those occurring in physiological conditions.

It is also important that, when needed, this effect of NO is immediate but also lasts for some time.

In general, the administration of NO can be useful in many pathophysiological conditions where vasodilatory and, in particular, peripheral action is required, for instance because of endothelial dysfunction.

Furthermore, the administration of NO can be beneficial also in situations where antimicrobial action is needed.

Nonetheless, to provide bioavailable NO, the molecule has to be stabilised because it is too reactive to reach the desired target within the body. Moreover, its use is made difficult by its very short half-life and its chemical nature as an unstable and reactive gas.

There are various known systems for releasing NO, in which it is produced or released at the time of use.

Known release methods typically involve polymers and small molecules such as S-nitroso-N-acetylpenicillamine and S-nitrosocysteine (CysNO), which release NO into the body.

These methods are not, however, able to provide sufficient quantities of NO for long periods of time or in a controlled manner since S-nitrosothiols, for example S-nitrosoglutathione (GSNO) and S-nitrosocysteine—natural NO donors—are particularly unstable in aqueous environment and in biological fluids (Moncada et al., 1993). In fact, formulations based on NO donors in solution typically decompose quantitatively within a few hours (Broniowska et al., 2012). Systems for the release of NO in aqueous media are disclosed in WO2010/086637, US2015/086651, WO2012/052561, U.S. Pat. No. 7,048,951.

Various systems for the topical administration of NO are also known.

For example, US2013089629 describes a kit for treating onychomycosis using NO comprising an acidifying agent to be used as pretreatment and a composition of nitrite and at least one polysaccharide with a sufficient amount of ascorbic acid to produce NO for use as a treatment.

U.S. Pat. No. 7,048,951 describes a system for the topical release of NO comprising an ointment composed of a non-aqueous medium and sodium nitrite, ascorbic acid and maleic acid as active ingredients which, when applied to the skin, release NO.

WO2008153762 describes a composition comprising an S-nitrosothiol, for example GSNO, in a pharmaceutical formulation that permits its long-term storage before administration to the patient.

WO1999044622 describes a topical formulation comprising nitric oxide, wherein the nitric oxide is generated when an acidifying agent and a nitric oxide donor come into contact at the site of action. The composition is used in the treatment of viral skin infections.

WO201102265 also describes gels for topical release of NO; such gels include functionalised polysiloxane macromolecules.

Some of these methods are also aimed at treating sexual dysfunction.

For example, US20130059017 describes a composition for topical delivery of nitric oxide to treat sexual dysfunction comprising a first phase comprising lecithin and nitric oxide and a second phase comprising an emulsifier, such that the nitric oxide is entrapped, for example through the formation of vesicles, and therefore remains intact. The second phase can also comprise polyglycols.

Various systems and solutions for releasing NO and therefore described in the prior art, intended in particular to deal with the problem of this compound's instability.

There is still a need for stable compositions, particularly for topical use, capable of releasing NO, when required, effectively and immediately, but at the same time capable of ensuring that NO is released for a sufficiently long period.

This problem is particularly heartfelt in the context of treatment for erectile dysfunction, in which immediate action that also lasts for a certain length of time is particularly desirable.

SUMMARY OF THE INVENTION

A stable formulation has now been found, which if need be permits the rapid release of nitrogen monoxide and at the same time the formation of S-nitrosothiol compounds, which by releasing NO more slowly and over an extended period, allow a longer period of action.

The kit that is the subject-matter of the present invention comprises:
  a) an anhydrous liquid phase comprising a solvent and at least one reducing agent, with the proviso that it is not a thiol;
  b) a solid phase comprising a nitrate and/or nitrite salt, copper ions and at least one thiol.

Said solvent is preferably selected from the group consisting of propylene glycol, glycerol, 1,3-propanediol and ethoxydiglycole. It is preferably propylene glycol.

Said reducing agent is preferably selected from ascorbic acid, fumaric acid, glycolic acid and maleic acid or mixtures thereof. Preferably, it consists of a mixture of fumaric acid and ascorbic acid.

Said thiol can be of natural or synthetic origin; it is preferably of natural origin.

The thiol is preferably selected from pantetheine and derivatives thereof, and alpha lipoic acid.

At the time of use, the two phases are combined, thus generating free nitric oxide and S-nitrosothiol (SNO) compounds.

Free nitric oxide can diffuse rapidly and has an immediate vasodilatory effect.

S-nitrosothiol compounds also have a local vasodilatory action and, above all, act as a system for slow release of NO.

The liquid formulation produced by combining the two phases is stable and active in releasing NO as soon as the two phases are mixed and for at least an hour afterwards.

The two phases (liquid and solid) are stable at room temperature for long periods as long as they are stored separately from one another. This therefore allows the kit to be stored for a long time until it is used, without losing efficacy.

In fact, the formulation of nitrites and/or nitrates in solid phase makes it possible to avoid any oxidation or loss of efficacy.

What is more, the solid phase formulation of thiols, containing easily oxidisable SH groups, prevents their oxidation and consequent loss of efficacy.

Furthermore, the use of natural compounds, such as propylene glycol or glycerol, thiols when of natural origin, and ascorbic and/or fumaric acid, ensures an excellent safety profile for both topical and systemic applications.

Propylene glycol and glycerol, when used as solvents, are advantageous in that they make the solid phase used soluble and at the same time allow administration of the product to a subject, owing to their high tolerability.

The reducing environment, generated by the reductant, allows free nitric oxide and S-nitrosothiol compounds with thiol to form in a few minutes.

Copper ions have a catalytic action that favours the formation of S-nitrosothiols.

All the components of the kit, as well as their formulation as a separate liquid phase and solid phase, have therefore been carefully selected to obtain a stable composition that can be stored for a long time without losing efficacy and which also, at the time of use, is capable of releasing NO with both immediate and prolonged effect.

The liquid formulation produced by combining the two phases is easy to administer, for example with a dropper or spray device.

Therefore, the use of the kit of the invention as a medicinal product is also a subject-matter of the present invention.

In particular, the kit of the invention can be used in all those pathophysiological situations in which the released nitrogen monoxide can act on the aetiology and pathogenesis the disorder, i.e. can improve its causes and/or clinical manifestations, for instance through its vasodilatory and/or antimicrobial activity.

For example, disorders that can be treated with the kit of the invention are selected from the group consisting of: male sexual dysfunction, angina, acne, alopecia, skin fissures, anal fissures, female sexual dysfunction, skin ulcers, wounds and skin aging.

The use of the kit for treating male sexual dysfunction, in particular erectile dysfunction is particularly preferred.

The kit is preferably administered topically. Systemic administration is, however, suitable.

A suitable container for storing the two phases, and mixing and administering them, is also a subject-matter of the present invention.

DETAILED DESCRIPTION OF THE INVENTION

Definitions

Within the context of the present invention, nitrogen monoxide and nitric oxide are synonymous and identify a compound with the molecular formula NO.

In the context of the present invention, the term glycerol refers to an organic compound with the IUPAC name propane-1,2,3-triol. Glycerol derivatives, such as glycerol, are also suitable for use in the present invention.

In the context of the present invention, propylene glycol and propane-1,2-diol are used synonymously.

In the context of the present invention, ethoxydiglycole and Transcutol® P are used synonymously.

In the context of the present invention, the term cysteamide refers to the molecule also known as β-alanyl-cysteamine or β-alethine.

In the context of the present invention, S-nitrosothiols (SNOs) are organic compounds, present both in the body (endogenous) and outside it (exogenous), which contain a nitroso group attached to the sulfur atom of a thiol.

In the context of the present invention, a thiol is an organic compound containing the SH group.

In the context of the present invention, the nitrite is the anion of $NO_2^-$ and the nitrate is the anion of formula $NO_3^-$.

The solid phase of the kit of the present invention comprises a nitrate and/or nitrite salt, copper ions and at least one thiol.

Any thiol can be used in the present invention.

In particular, thiol can be of plant or synthetic origin.

Thiols of plant origin are preferred because of their greater tolerability.

Examples of thiols suitable for use in the present invention are: pantetheine, alpha-lipoic acid, phosphopantetheine, cysteine, homocysteine, thioglycolic acid, β-mercaptopropionic acid, β-mercaptoethanol, β-thioethanolamine, coenzyme A, cysteamide, γ-glutamylcysteine, phytochelatin, trypanothione, captopril, glutathione and N-acetylcysteine.

All of these thiols are commercially available or can be synthesised by procedures known in the art.

The thiol is preferably selected from pantetheine and derivatives thereof, and alpha lipoic acid and derivatives thereof.

Alpha lipoic acid has the following structural formula:

Diagram 1: alpha lipoic acid (reduced form)

Derivates of pantetheine are, for example, coenzyme A, phosphopantetheine and cysteamide. The relevant structural formulae are illustrated in Diagram 2 below.

Diagram 2. Formula for pantetheine and derivatives thereof. The compounds are classified as follows: 1-5: coenzyme A, 2-5: phosphopantetheine, 3-5: pantetheine, 4-5: cysteamide.

Various types of nitrite or nitrate salts can be used. Those generally used are inorganic salts, for example salts with sodium, potassium, lithium, magnesium, manganese, calcium, strontium, barium, silver, copper, iron, zinc, nickel, cadmium, cobalt, aluminium, caesium, ammonium or tetraethylammonium ions. Salts with sodium or potassium ions are preferred.

In a preferred embodiment, the solid phase contains sodium nitrite and/or potassium nitrite.

The copper ions can be present in the solid phase in a free or complexed form. For example, they can be present in the form of salts, for example sulfate or acetate salts, or as an edetate or as a complex with peptide or protein derivatives. For example, copper can be in a form complexed with the peptide GHK (glycyl-L-histidyl-L-lysine).

The liquid phase of the kit of the invention comprises a solvent and at least one reducing agent.

The solvent is preferably selected from propylene glycol, glycerol, 1,3-propanediol and ethoxydiglycole. Their derivatives, such as glycerol, are equally suitable.

The reducing agent is preferably selected from ascorbic acid, fumaric acid, glycolic acid and maleic acid or a mixture thereof. Other biologically acceptable acids are equally suitable.

In a preferred embodiment, the reducing agent consists of a mixture of ascorbic acid and fumaric acid.

Preferably, phase a) of the kit (liquid phase) comprises solvent in an amount of between 80 and 99.9 wt. % and reducing agent in an amount of between 0.1 and 20 wt. %. More preferably, phase a) of the kit (liquid phase) comprises solvent in an amount of between 80 and 99 wt. % and reducing agent in an amount of between 1 and 20 wt. %.

In a preferred embodiment, phase a) comprises 98 wt. % solvent and 2 wt. % reducing agent.

In an even more preferred embodiment, said reducing agent comprises ascorbic acid in an amount of between 0.2 and 1 wt. % and fumaric acid in an amount of between 1 and 1.8 wt. %.

Preferably, phase b) of the kit (solid phase) comprises a thiol, an up to twofold molar excess of nitrite and/or nitrate over the thiol, and a molar amount of copper ions up to 50 times less than the thiol. Still more preferably, for every mole of thiol, between 1 and 2 moles of nitrite and/or nitrate ions and between 0.02 and 0.5 moles of copper ions are present. In a particularly preferred embodiment, the molar ratio between thiol, nitrite and/or nitrate ions and copper ions amounts, respectively, to 1:1.5:0.1.

Preferably, the mixture produced by mixing the two phases comprises 80-99% of liquid phase and 1-20% of solid phase.

The liquid phase (a) of the kit is prepared by mixing the solvent with the reducing agent or agents.

The solid phase (b) is prepared by mixing the various components, preferably in powder form.

All the individual components of the two phases are known and easily available commercially.

The two phases are mixed at the time of use, preferably at room temperature.

The solution just mixed therefore contains the solvent, the reducing agent or agents, thiol, nitrite and/or nitrate ions and copper ions.

Nitrite and/or nitrate ions are consumed rapidly. At the same time, the nitrogen monoxide is produced rapidly and, owing to the catalytic action of the copper ions, an S-nitroso compound of the thiol in the solid phase is formed. This compound remains stable for over 1 hour from its formation. The S-nitrosothiol compound has a vasodilatory action and releases NO, allowing it to act more slowly and over a more extended period than free NO.

The formulation of the invention, in two separate phases with the specific components mentioned above, therefore has the notable advantage of allowing the rapid formation of nitrogen monoxide in a rapidly diffusible form and, at the same time, the formation of S-nitrosothiol compounds that are sufficiently stable for sustained release of NO over time.

In a preferred embodiment, the kit of the invention comprises:
a) a liquid phase comprising propylene glycol as solvent, and ascorbic acid and fumaric acid as reductants;
b) a solid phase comprising sodium or potassium nitrite, copper ions and reduced pantetheine.

By combining the two phases, therefore, free NO and S-nitroso compounds of pantetheine are produced.

In another preferred embodiment the kit of the invention comprises:
a) a liquid phase comprising propylene glycol as solvent, and ascorbic acid and fumaric acid as reductants;
b) a solid phase comprising sodium or potassium nitrite, copper ions and reduced alpha lipoic acid.

By combining the two phases, therefore, free NO and S-nitroso compounds of alpha lipoic acid are produced.

In an even more preferred embodiment, the reaction mixture is prepared by dissolving 10 mM fumaric acid and between 30 and 50 mM ascorbic acid in 5 mL propylene glycol. A solid phase, consisting of a mixture of pantetheine, sodium nitrite and powdered copper sulfate, is added to the solution obtained in such a quantity that their concentration in the final reaction volume is equal to: pantetheine 10 mM, sodium nitrite 15 mM; copper sulfate 1 mM. Mixing is done at room temperature (about 25° C.). The solution just mixed contains propylene glycol, ascorbic acid, pantetheine, fumaric acid, sodium nitrite and traces of copper sulfate.

In another preferred embodiment, the reaction mixture is prepared by dissolving 10 mM fumaric acid and between 30 and 50 mM ascorbic acid in 5 mL propylene glycol. A solid phase, consisting of a mixture of alpha lipoic acid, sodium nitrite and powdered copper sulfate, is added to the solution obtained in such a quantity that their concentration in the final reaction volume is equal to: alpha lipoic acid 10 mM, sodium nitrite 15 mM; copper sulfate 1 mM. Mixing is done at room temperature (for example 25° C.). The solution just mixed contains propylene glycol, ascorbic acid, alpha lipoic acid, fumaric acid, sodium nitrite and traces of copper sulfate.

A container containing the kit of the invention is also a subject-matter of the invention. Said container can be composed of a first section that anhydrously houses the solid, typically powdered, mixture of nitrite and/or nitrate salts, copper ions and thiol, and a second section housing the solvent in a reducing environment provided by the reducing agent Said container is configured such that, at the time of use, the contents of the first section are released into the second section, so that the free NO and the S-nitrosothiol adducts are formed and are released within a few minutes. For example, there may be a dispensing button, which when pressed releases the solid phase into the liquid phase, starting the reaction. Alternatively, there can be a double nozzle through which, by pressure, the two phases emerge and mix before being applied through a common nozzle.

The two phases, packed separately, can thus be stored for long periods, as long as they are protected from light and oxygen.

In a preferred embodiment, this container is in the form of a spray dispenser.

In another embodiment, it is a dropper device.

In another embodiment, the kit of the invention is contained in a transdermal patch in which the two phases are kept separate, for example on superimposed layers, and mixed at the time of application, for example by means of a suitable button, thus releasing nitric oxide and S-nitrosothiol onto the skin.

In any case, any other configuration of container comes within the scope of the present invention as long as it is suitable for containing the two separate phases.

The kit can be administered in any suitable way, for example topically, systemically, sublingually, nasally, vaginally or rectally.

Preferred routes of administration are the topical and sublingual routes. Topical application is particularly preferred in cases where a local vasodilatory effect is sought, for example in treating erectile dysfunction.

The kit can also comprise other active ingredients, such as antibiotics, analgesics, anti-inflammatory agents, vasodilators or vasoconstrictors, UV ray protectors, antihistamines, hormones, cardiovascular agents, lubricants, antiseborrhoeic agents, cleansing agents, deodorants, disinfectants, emollients and so on, which may be duly selected by the person skilled in the art depending on the desired effect.

The kit can also comprise other pharmacologically acceptable components, for example preservatives, stabilisers or excipients as appropriate.

The simplicity of manufacture, application and use of the kit constitutes a further advantage of the invention.

The use of the kit of the invention as a medicinal product is also a subject-matter of the present invention.

In particular, the kit of the invention can be used in all clinical situations in which released NO can act on the aetiology and pathogenesis of the disorder, i.e. on its cause and/or its clinical manifestations. Persons skilled in the art can easily, based on common knowledge of the field, identify the pathophysiological situations that might benefit from administration of NO. In particular, these may be situations where a vasodilatory action is sought, in particular locally, or an antimicrobial one.

For example, the kit of the invention can advantageously be used for the following disorders: angina, because of the vasodilatory effect of NO; acne, because of the antimicrobial effect of NO (Qin et al., 2015); alopecia, which benefits from increased microcirculation in the region in question (Namazi et al., 2003); skin fissures and anal fissures, where NO facilitates inversion of the state of hypertonus and muscle collapse, thereby assisting with local healing (Schouten et al., 1996); female sexual dysfunction, where NO promotes an increase in the vascularisation of the clitoris (Souto et al., 2011); scalds, burns, skin ulcers or wounds, owing to the antibacterial and re-epithelisation action of NO; skin aging, for example because NO contributes to decreased hypertonus of the muscles responsible for expression in the region of the eyes; male sexual dysfunction, owing to the vasodilatory effect of NO on the endothelial walls of the blood vessels.

Preferably, the kit is used for treating male sexual dysfunction, in particular erectile dysfunction.

In such a case, the kit can conveniently also include antibiotics, spermicides, agents that stimulate erection or other similar additives.

The term erectile dysfunction means the male subject's inability to achieve and/or maintain a sufficient erection to lead to satisfactory intercourse.

Erectile dysfunctions can be of primary or secondary type. Secondary dysfunctions can have organic, for instance endocrine, vascular, neurological and/or psychiatric causes. Such dysfunctions can result from other disorders, for example dyslipidaemia, obesity, type 1 and 2 diabetes, metabolic diseases; or they can result from drug or substance abuse or from medical treatments. Therefore, the kit of the invention can also be used for treating secondary-type erectile dysfunction, in particular that resulting from dyslipidaemia, obesity, type 1 and 2 diabetes, metabolic diseases, drug or substance abuse, or medical treatments.

In the treatment of erectile dysfunction, the kit is preferably administered topically. This has the advantage of preventing the risks and problems connected with the systemic administration of compounds.

Furthermore, this type of application has the advantage that it is easy to measure out the necessary amount of product immediately. This is particularly important in the case of erectile dysfunction.

Persons skilled in the art, for example doctors, are able to assess the dosage and usage times of the kit depending on the subject's condition, the disorder and other relevant parameters, based on their general knowledge in the field.

The present invention will now be illustrated further by the following examples.

EXAMPLES

Example 1

Preparation of the Reaction Mixture and Analysis of the Solution Obtained

The reaction mixture is prepared by dissolving the following amounts of reagents in 5 mL propylene glycol: fumaric acid 10 mM; ascorbic acid between 30 and 50 mM (PHASE A).

A solid phase, consisting of a mixture of pantetheine, sodium nitrite and powdered copper sulfate, is added rapidly to the solution obtained, in a quantity such that their concentration in the final reaction volume amounts to: pantetheine 10 mM, sodium nitrite 15 mM; copper sulfate 1 mM (PHASE B). Mixing is done at room temperature (25° C.) (Fukuto et al., 2013).

Figure 1:
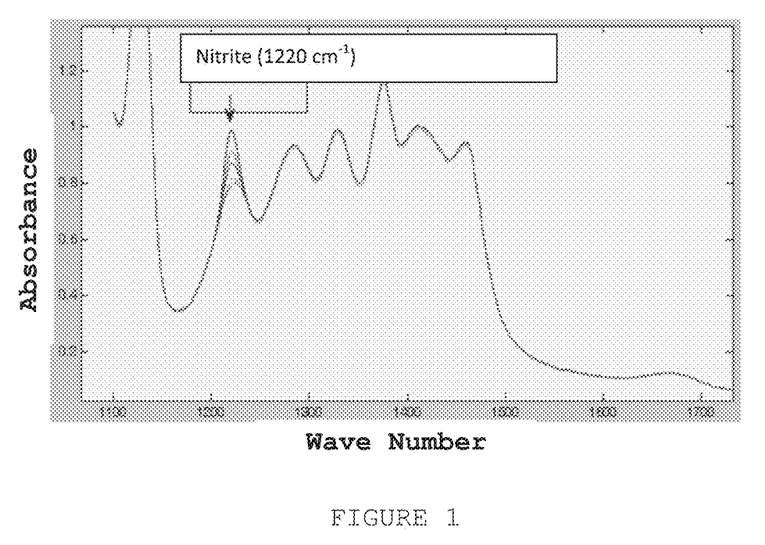
FIG. 1 is an infrared absorption spectrum of the mixed solution. The peak corresponding to nitrites is visible at 1220 cm$^{-1}$.

The consumption of sodium nitrite after mixing has been measured following peak infrared absorption at 1220 cm$^{-1}$ relative to the nitrite remaining in solution (FIG. 1).

The solution just mixed contains propylene glycol, ascorbic acid, pantetheine, fumaric acid, sodium nitrite and traces of copper sulfate. The spectra measured in succession demonstrate that the nitrite present was completely consumed within about 20 minutes of mixing.

By analysing the visible UV absorption spectrum of the mixed solution, incubated at room temperature for 60 min (FIG. 2) it is noted that the absorption spectrum (solid line) reveals a maximum of 548 nm, corresponding to the formation of an S-nitroso compound, which was absent when the phases were mixed (broken line, spectrum recorded at time zero) (Seidler et al., 2002; Smith et al., 2012).

Figure 2:
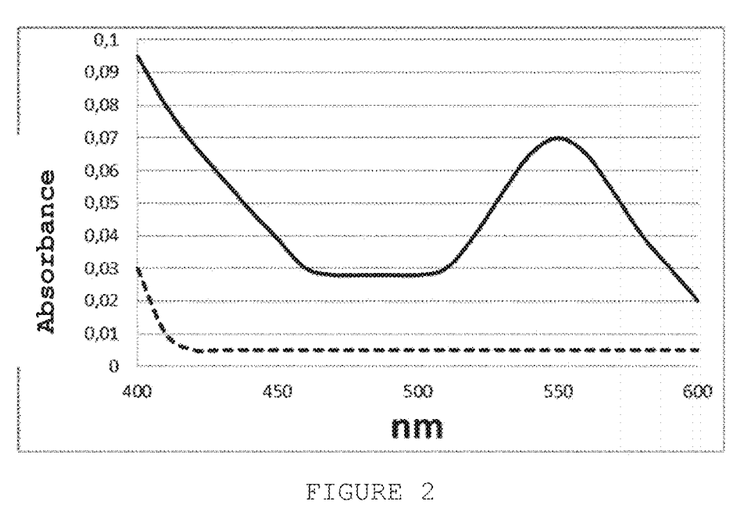
FIG. 2 is a formation of nitrosothiol after mixing of phases A and B. Solid line: visible UV absorption spectrum of the solution mixed and incubated at room temperature for 60 min; a maximum of 548 nm can be seen, corresponding to the formation of an S-nitroso compound. Broken line: spectrum recorded at time zero.

The S-nitroso compound observed, which was absent when the phases were mixed, is attributable to the S-nitroso pantetheine derivative.

The reaction that provides for alpha lipoic acid as the use of a SH group donor gives comparable results.

The experimental data obtained, illustrated in FIGS. 1 and 2, demonstrate that the simple and stable formulations of phases A and B allow a homogeneous phase to form after mixing, in which nitrogen monoxide is rapidly produced by direct decomposition of the nitrite present in solution. At the same time, owing to the catalytic action of the traces of copper present, the corresponding nitrosothiol is also formed, and remains sufficiently stable for more than 1 hour at room temperature. Therefore, this formulation allows the rapid formation of nitrogen monoxide in a rapidly diffusible form and, at the same time, the formation of nitrosothiol that is sufficiently stable for the sustained release of nitrogen monoxide over time.

Example 2

In-Vitro Study of the Effect of the Formulation

To check the role performed by the endogenous release of NO on vascular smooth muscle, we repeated the numerous experimental and clinical works described in the literature: a specific and exhaustive review is given by the following work: Nitric oxide and penile erectile function (Noboru Toda T, Kazuhede Ayajki, Tomio Okamura; Pharmacology Therapeutics 106 (2005) 233-266).

This work was selected because the penile erection model adapts well, even experimentally, to in-vitro observations in animals and humans.

In particular, this model is used for planning experiments aimed at checking the vasodilatory action of NO on vascular smooth muscle cells, since the methodology presented by the authors allows samples of corpus cavernosum tissue to be obtained from rats, on which studies of response to various exogenous molecules can be conducted, to detect their relaxation/contraction effects on smooth muscle cells.

The work we selected and the experimental model on which we based our observations can easily be traced in the following work: G. Italiano, A. Calabrò and F. Pagano of the Urology Institute of Padua University, published in Pharmacology Therapeutics (Vol 30 no 4, 1994 pp. 325-334).

Preparation of the Tissue Samples from the Corpora Cavemosa of Rats

We used 20 adult Wistar-type rats weighing between 175 and 200 g; after having sacrificed the rats we obtained corpus cavernosum tissues as described by the methods and placed these in a Krebs solution (in mM: 118 NaCl, 4.7 KCl, 1.2 $KH_2PO_4$, 1.2 $MgSO_4$, 1.5 $CaCl_2$, 25 $NaHCO_3$, 11 glucose).

A single sample was taken from each rat.

The excised tissues were then put in 10 mL Krebs solution and held in place by two metal arms to allow assessment of any changes in the forces observed and assessed by the Grass FT03 model (using a force displacement transducer apparatus to assess the muscle tension of tissues, calibrated in mN). The saline solution containing the tissues (Krebs solution) was kept at pH 7.4±0.1 and at 37° C., with oxygenation using a mixture of 95% oxygen and 5% carbon dioxide.

Figure 3:
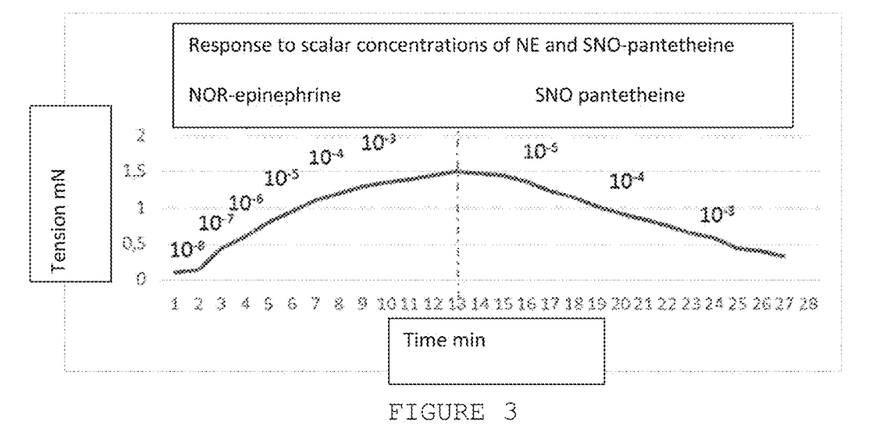
FIG. 3 is a response to scalar concentrations of norepinephrine (NE) and SNO-pantetheine.
Figure 4:
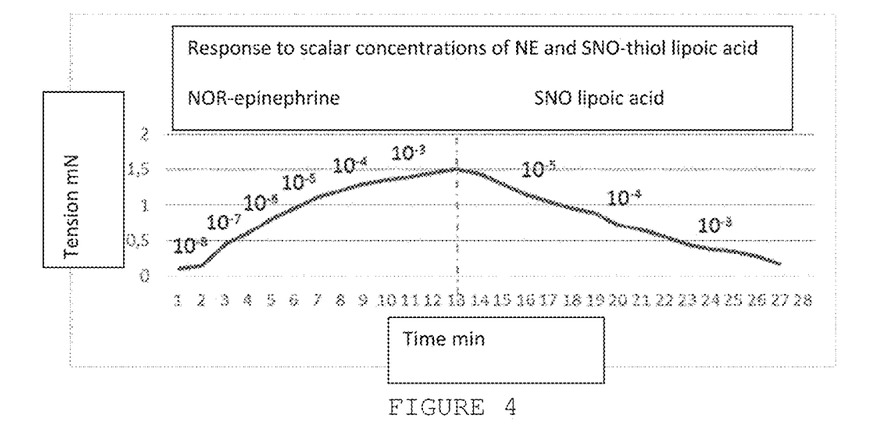
FIG. 4 is a response to scalar concentrations of norepinephrine (NE) and S-nitrosothiol of lipoic acid.

Scalar solutions of norepinephrine ($10^{-8}$ M to $10^{-3}$ M) were added to these preparations to produce constriction of about 1.5 mN; subsequently, scalar solutions of S-nitrosothiol of pantetheine ($10^{-8}$ M to $10^{-3}$ M) were added, revealing a corresponding relaxation of the tissue of the corpora cavemosa such that the effect of the norepinephrine was cancelled out (see FIG. 3); furthermore, we added the S-nitrosothiol of alpha lipoic acid to five samples of corpora cavemosa prepared by the same method seen above, and in FIG. 4 behaviour that is very similar to that of the S-nitrosothiol of pantetheine can be seen.

In conclusion, this experiment demonstrated that S-nitrosothiols, such as the S-nitrosothiol of pantetheine and the S-nitrosothiol of alpha lipoic acid, exhibit the desired vasodilatory effect on the smooth muscle of the corpora cavemosa of rats.

Example 3

In-Vivo Test of Sexual Function in Diabetic Rat Models

Next we tested the possible beneficial effects of SNO-pantetheine on sexual function in a rat model with type 1 diabetes induced by streptozotocin, which is typically accompanied by deficit of sexual activity.

In short, male Wistar rats were assigned to a cage (45× 50×35 cm) covered in glass and lit with red light. Training took place every day after 5 pm for about 30 min, and after 10 minutes of acclimatization a female rat in an oestrogenic phase was introduced into the cage. We then observed the sexual behaviour of diabetic rats vs. the relevant controls by measuring standard parameters (Burnett et al., 1995).

As can be seen in Table 1, the topical application of SNO-pantetheine is able to induce an increase in sexual behaviour in the diabetic rat model vs. all the parameters assessed (Agmo et al., 1997).

| Sexual behaviour | Normal rat Control | | Diabetic rat Control | | SNO-pantetheine | |
|---|---|---|---|---|---|---|
| | Day 0 | Day 30 | Day 0 | Day 30 | Day 0 | Day 30 |
| ML (seconds) | 40.7 ± 4.8 | 42.3 ± 2.5 | 42.6 ± 3.8 | 133.2 ± 5.3* | 42.5 ± 2.9 | 34.3 ± 2.5* |
| IL (seconds) | 46.4 ± 3.8 | 44.7 ± 3.0 | 58.1 ± 5.1 | 172.2 ± 6.5* | 52.3 ± 3.9 | 44.7 ± 4.2* |
| EL (seconds) | 411.7 ± 12.7 | 405.3 ± 11.3 | 411.8 ± 13.2 | 306.2 ± 8.6* | 423.2 ± 12.5 | 375.8 ± 10.8* |
| MF (number) | 8.3 ± 1.1 | 9.1 ± 0.9 | 13.2 ± 1.3 | 5.1 ± 0.9* | 12.0 ± 1.7 | 11.2 ± 0.3* |
| IF (number) | 13.0 ± 1.4 | 10.8 ± 1.8 | 11.4 ± 0.7 | 4.4 ± 0.3* | 11.2 ± 0.9 | 14.5 ± 0.8* |
| PEI (seconds) | 363.3 ± 10.5 | 369.2 ± 12.1 | 331.7 ± 5.9 | 865.5 ± 13.6* | 343.3 ± 10.9 | 386.2 ± 14.3* |

ML = Mating latency; IL = Introduction latency; EL = Ejaculation latency; MF = Mating frequency; IF = Introduction frequency; PEI = Post-ejaculatory interval.
*P < 0.05

Example 4

Study of the Effect of the Formulation on Healthy Volunteers

We took 10 healthy male volunteers in a good state of health aged between 48 years and 70 years (mean 60 years).

We also accepted smokers as long as they did not exceed 10 cigarettes daily.

We excluded patients with hypertension, even if controlled, and also obese patients, patients with type 1 and 2 diabetes or with neuropsychiatric disorders, and those with chronic diseases, who were therefore under continuing treatment.

We obtained written consent from them and gave them an inclusion test using the International Index of Erectile Function, formed of a self-administered questionnaire with 15 questions and answers amended by us and limited to questions 1, 2, 3, 4, 5 and 15 for specific assessment of erectile function.

The questions and answers used for the test follow.
Questions
Question 1: How often were you able to get an erection during sexual activity?
Question 2: When you had erections with sexual stimulation, how often were your erections hard enough for penetration?
Question 3: When you attempted intercourse, how often were you able to penetrate (enter) your partner?
Question 4: During sexual intercourse, how often were you able to maintain your erection after you had penetrated (entered) your partner?
Question 5: During sexual intercourse, how difficult was it to maintain your erection to completion of intercourse?
Question 15: How do you rate your confidence that you could get and keep an erection?
Scoring and Assessment
Questions 1, 2, 3, 4: 0=No sexual activity; 1=Almost never/never; 2=A few times; 3=Sometimes; 4=Most times; 5 Almost always/always
Question 5: 0=Did not attempt intercourse; 1=Extremely difficult; 2=Very difficult; 3=Difficult; 4=Slightly difficult; 5=Not difficult
Question 15: 1=Very low or practically zero; 2=Low; 3=Moderate; 4=High; 5=Very high Observation continued for 30 days and at the end the enrolees self-assessed themselves with a second, final, post-treatment test, again on questions 1, 2, 3, 4, 5 and 15.

The selected patients had to use the spray (one vial) a few minutes before each intercourse (but not more than twice a day) with their normal partner.

Figure 5:
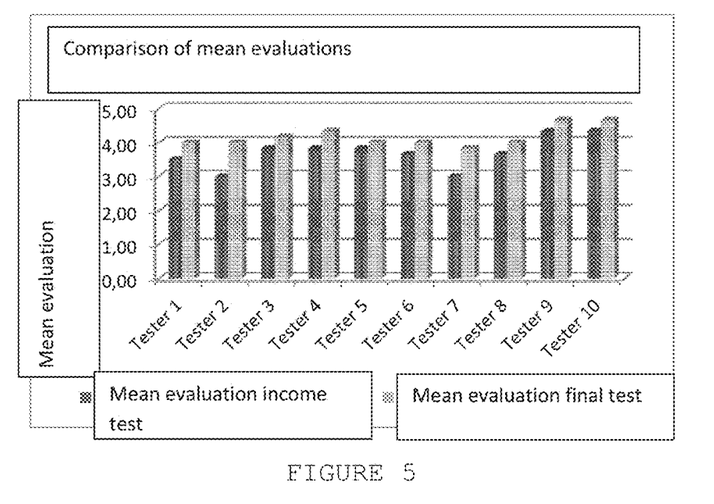
FIG. 5 is a Study of the effect of the formulation on healthy volunteers; comparison of the mean evaluations before and after the use of the formulation.

The data and the statistical significance are recorded below in Tables 2 and 3, and in FIG. 5.

In conclusion, this experiment showed the tolerability of the kit of the invention in humans and its ease of use.

BIBLIOGRAPHICAL REFERENCES

Rajfer J, Aronson W J, Bush P A, Dorey F J, Ignarro. N Engl J Med. 1992 Jan. 9; 326(2):90-4.31 Nitric oxide as a mediator of relaxation of the corpus cavemosum in response to nonadrenergic, noncholinergic neurotransmission.
Fulton D, Gratton J P, Sessa W C. Post translational control of endothelial nitric oxide sinthase: why isn't calcium/calmoduline enough? The Journal of Pharmacology and Experimental Therapeutics 2001, 220:815-61.
Furchgott R F, Zawadski J V. The obligatory role of endothelial cells in the relaxation of arterial smooth muscle by acetylcholine. Nature 1980; 288:373-6.
Palmer R M J, Ferrige A G, Moncada S. Nitric oxide release accounts for the biological activity of endothelial-derived relaxing factor. Nature 1987; 327:524-6.
Cayatte A J, Palacino J J, Horten K, Cohen R A. Chronic inhibition of nitric oxide production accelerates neointima formation and impairs endothelial function in hypercholesterolemic rabbits. Arterioscler Thromb 1994; 14:753-9.
Moncada S, Higgs A. The L-arginine-nitric oxide pathway. N Engl J Med 1993; 329:2002-12.
Marietta M A. Nitric oxide synthase structure and mechanism. J Biol Chem 1993; 268:12231-4.
Pharmacology Therapeutics 106 (2005): 233-266.
Ignarro L J. Endothelium-derived nitric oxide: actions and properties. FASEB J 1989, 3:31-6

TABLE 2

Results of the inclusion test

| Question | Tester 1 | Tester 2 | Tester 3 | Tester 4 | Tester 5 | Tester 6 | Tester 7 | Tester 8 | Tester 9 | Tester 10 |
|---|---|---|---|---|---|---|---|---|---|---|
| Q 1 | 4 | 3 | 5 | 3 | 4 | 3 | 3 | 4 | 5 | 4 |
| Q 2 | 4 | 3 | 4 | 4 | 4 | 4 | 3 | 3 | 5 | 4 |
| Q 3 | 3 | 3 | 3 | 4 | 3 | 4 | 3 | 3 | 4 | 4 |
| Q 4 | 4 | 3 | 3 | 4 | 4 | 3 | 3 | 4 | 4 | 4 |
| Q 5 | 3 | 3 | 4 | 4 | 4 | 4 | 3 | 4 | 4 | 5 |
| Q 15 | 3 | 3 | 4 | 4 | 4 | 4 | 3 | 4 | 4 | 5 |
| Mean | 3.50 | 3.00 | 3.83 | 3.83 | 3.83 | 3.67 | 3.00 | 3.67 | 4.33 | 4.33 |

TABLE 3

Results of the final test

| Question | Tester 1 | Tester 2 | Tester 3 | Tester 4 | Tester 5 | Tester 6 | Tester 7 | Tester 8 | Tester 9 | Tester 10 |
|---|---|---|---|---|---|---|---|---|---|---|
| Q 1 | 4 | 4 | 5 | 4 | 4 | 4 | 3 | 4 | 5 | 5 |
| Q 2 | 4 | 4 | 4 | 5 | 4 | 4 | 4 | 4 | 5 | 4 |
| Q 3 | 4 | 4 | 4 | 5 | 4 | 4 | 4 | 4 | 4 | 5 |
| Q 4 | 4 | 4 | 4 | 4 | 4 | 4 | 4 | 4 | 5 | 4 |
| Q 5 | 4 | 4 | 4 | 4 | 4 | 4 | 4 | 4 | 4 | 5 |
| Q 15 | 4 | 4 | 4 | 4 | 4 | 4 | 4 | 4 | 5 | 5 |
| Mean | 4.00 | 4.00 | 4.17 | 4.33 | 4.00 | 4.00 | 3.83 | 4.00 | 4.67 | 4.67 |

One-Tailed T-Test for Paired Samples
Q 1, P=0.018
Q 2, P=0.018
Q 3, P=0.0001
Q 4, P=0.002
Q 5, P=0.04
Q 15 P=0.018

Moncada S, Higgs A. The L-arginine-nitric oxide pathway. N Engl J Med 1993; 329:2002-12.
Broniowska K A, Hogg N. The chemical biology of S-nitrosothiols. Antioxid Redox Signal. 2012, 17:969-80.
Fukuto J M, Cisneros C J, Kinkade R L. A comparison of the chemistry associated with the biological signaling and actions of nitroxyl (HNO) and nitric oxide (NO). J Inorg Biochem. 2013, 118:201-8.

Seidler M, Uckert S, Waldkirch E, Stief C G, Oelke M, Tsikas D, Sohn M, Jonas U. In vitro effects of a novel class of nitric oxide (NO) donating compounds on isolated human erectile tissue. Eur Urol. 2002, 42:523-8.

Smith B C, Marietta M A. Mechanisms of S-nitrosothiol formation and selectivity in nitric oxide signaling. Curr Opin Chem Biol. 2012, 16:498-506.

Noboru Toda T, Kazuhede Ayajki, Tomio Okamura; Pharmacology Therapeutics 106 (2005) 233-266)

G. Italiano, A. Calabrd, F. Pagano. Pharmacologic Therapeutics Vol 30, No 4, pp. 325-33.

Burnett A. Biology of Reproduction 52, 485-489 (1995). Agmo A. Male rat sexual behavior. Brain Res Protoc. 1997; 1:203-9.

Schouten W R, Briel J W, Auwerda J J, Boerma M O. Anal fissure: new concepts in pathogenesis and treatment. Scand J Gastroenterol Suppl. 1996; 218:78-81.

Qin M, Landriscina A, Rosen J M, Wei G, Kao S, Olcott W, Agak G W, Paz K B, Bonventre J, Clendaniel A, Harper S, Adler B L, Krausz A E, Friedman J M, Nosanchuk J D, Kim J, Friedman A J. Nitric Oxide-Releasing Nanoparticles Prevent *Propionibacterium acnes*-Induced Inflammation by Both Clearing the Organism and Inhibiting Microbial Stimulation of the Innate Immune Response. J Invest Dermatol. 2015 Jul. 14. doi: 10.1038/jid.2015.277.

Souto S, Palma P, Fregonesi A, Palma T, Reis L O. Vascular modifications of the clitoris induced by topic nitric oxide donor gel-preliminary study. J Sex Med. 2011 February; 8(2):484-8. doi: 10.1111/j.1743-6109.2010.02045.x.

Namazi M R. Nitric oxide donors as potential additions to anti-alopecia areata armamentarium. Inflamm Res. 2003 June; 52(6):227-9. Review.

What is claimed is:

1. A kit comprising:
   a) an anhydrous liquid phase comprising a solvent and at least a reducing agent, with the proviso that it is not a thiol;
   b) a solid phase comprising at least a nitrate and/or nitrite salt, copper ions and at least a thiol, wherein said thiol is of natural origin.

2. The kit according to claim 1 wherein said thiol is selected from pantetheine, alpha lipoic acid, coenzyme A, phosphopantetheine and cysteamide.

3. The kit according to claim 1 wherein said solvent is selected from propylene glycol, glycerol, 1,3-propanediol and ethoxydiglycole.

4. The kit according to claim 1, wherein said reducing agent is selected from ascorbic acid, fumaric acid, glycolic acid and maleic acid or mixtures thereof.

5. The kit according to claim 1, wherein said nitrite salt is sodium nitrite or potassium nitrite.

6. The kit according to claim 1, wherein said copper ions are present as salts or as a complex with peptide or protein derivatives.

7. The kit according to claim 1, wherein said phase a) comprises said solvent in an amount comprised between 80 and 99.9% by weight and said reducing agent in an amount comprised between 0.1 and 20% by weight.

8. The kit according to claim 7, wherein said reducing agent comprises ascorbic acid in an amount comprised between 0.2 and 1% by weight and fumaric acid in an amount comprised between 1 and 1.8% by weight.

9. The kit according to claim 1 wherein said phase b) comprises said thiol, said nitrite and/or nitrate in molar excess up to two times compared with the thiol and said copper ions in a lower molar amount up to 50 times compared with the thiol.

10. The kit according to claim 9, wherein for each thiol mole, from 1 to 2 moles of nitrite and/or nitrate and from 0.02 to 0.5 moles of copper ions are present.

11. The kit according to claim 10, wherein the molar ratio between thiol, nitrite and/or nitrate and copper ions is, respectively, 1:1.5:0.1.

12. The kit according to claim 1, wherein the mixture obtained from the mixing of the two phases comprises 80-99% of liquid phase and 1-20% of solid phase.

13. The kit according to claim 1, for use as a medicament.

14. The kit for the use according to claim 13, for the treatment of a disease selected from the group consisting of: male sexual dysfunction, in particular erectile dysfunction, angina, acne, alopecia, fissures, anal fissure, female sexual dysfunction, burns, skin ulcers, wounds, skin aging, sexual dysfunction of secondary type and deriving from a pathological condition selected from dyslipidemia, obesity, diabetes of type I and II, metabolic disease or from the use of drugs or abuse drugs or from medical treatments.

* * * * *